United States Patent [19]

Giddings

[11] Patent Number: 4,737,268

[45] Date of Patent: Apr. 12, 1988

[54] THIN CHANNEL SPLIT FLOW CONTINUOUS EQUILIBRIUM PROCESS AND APPARATUS FOR PARTICLE FRACTIONATION

[75] Inventor: John C. Giddings, Salt Lake City, Utah

[73] Assignee: University of Utah, Salt Lake City, Utah

[21] Appl. No.: 840,760

[22] Filed: Mar. 18, 1986

[51] Int. Cl.[4] .......................... B03B 7/00; B03C 5/00
[52] U.S. Cl. .................................... 209/12; 209/127.1;
209/129; 209/131; 209/210; 209/422; 210/748
[58] Field of Search ................... 209/1, 2, 12, 18, 39,
209/40, 127.1, 129, 131, 132, 155, 156, 208, 210,
422, 478, 493, 494; 210/222, 223, 243, 695, 748

[56] References Cited

U.S. PATENT DOCUMENTS

| | | | |
|---|---|---|---|
| 453,317 | 6/1891 | Townsend | 209/478 X |
| 3,449,938 | 6/1969 | Giddings | 210/775 X |
| 3,482,692 | 12/1969 | Postma | 209/156 |
| 3,511,776 | 5/1970 | Avampato | 210/748 X |
| 4,102,780 | 7/1978 | Sun et al. | 209/39 |
| 4,214,981 | 7/1978 | Giddings | 209/155 |
| 4,250,026 | 2/1981 | Giddings et al. | 209/156 X |
| 4,284,498 | 8/1981 | Grant et al. | 209/155 |
| 4,555,933 | 12/1985 | Johnston | 209/129 X |

FOREIGN PATENT DOCUMENTS

| | | | |
|---|---|---|---|
| 0528091 | 11/1921 | France | 209/422 |
| 0898197 | 4/1945 | France | 209/422 |
| 0143744 | 7/1961 | U.S.S.R. | 209/131 |

Primary Examiner—R. B. Reeves
Assistant Examiner—Edward M. Wacyra

[57] ABSTRACT

A thin channel split flow process for particle fractionation which effects a rapid and efficient separation of the particles comprising introducing a stream of fluid containing the particles to be separated into the inlet end of a thin enclosed channel whose transverse dimension is very small, applying a special field or gradient or combination thereof transversely across the thin dimension of the channel to create a driving force a component of which is perpendicular to the main flow plane, adjusting the flow rate to achieve laminar flow conditions throughout the channel to allow the particles under the influence of the field/gradient to segregate into different stream laminae as they approach different transverse equilibrium positions, splitting the channel stream at the outlet end into substreams containing different separated fractions of the particles in the initial mixture, recovering the substream and thereby recovering the separated fractions.

25 Claims, 2 Drawing Sheets

THIN CHANNEL SPLIT FLOW CONTINUOUS EQUILIBRIUM PROCESS AND APPARATUS FOR PARTICLE FRACTIONATION

BACKGROUND OF THE INVENTION

This application is related to my copending patent application Ser. No. 822,529, filed Jan. 27, 1986.

1. Field of the Invention

This invention relates to a new process for particle fractionation. More particularly, the invention relates to a new process for fractionation of particulate or molecular components and/or concentration or purification of said components according to size or to other physical characteristics, and to a new type of apparatus for accomplishing the same.

Specifically, the invention provides a new continuous and rapid process for separation of particulate or molecular components which have different equilibrium positions or distributions across the thickness of a thin channel. The new process broadly comprises introducing a stream of fluid containing the particulate or molecular components to be separated or concentrated into the inlet end of a thin enclosed channel whose transverse dimension is very small, preferably much smaller than the other two dimensions, applying a special field or gradient or combination thereof transversely across the thin dimension of the channel to create a driving force a component of which is perpendicular to the main flow plane, adjusting the flow rate to achieve laminar flow conditions throughout the channel or at least throughout a sufficient portion of the channel immediately preceding the outlet end to allow the particulate or molecular components under the influence of the field/gradient to wholly or partially segregate into different stream laminae as they approach different transverse equilibrium positions, splitting the channel stream at the outlet end into substreams containing different separated purified or concentrated fractions of the particulate or molecular components in the sample mixture, recovering the substream and thereby recovering the separated or concentrated fractions of the initial mixture.

As a special embodiment, the invention further provides a process for separating or concentrating particulate or molecular components using at least one of the above-described thin channels linked to one or more additional channels of the same or different type wherein the channels are joined by fluid streams in which one or more of the outlet streams from one or more channels is fed to the inlet stream of one or more other channels.

The invention further provides a new type of separation apparatus for use in the above-noted process which comprises one or more special thin channels or cells which permits one to effect the above-noted rapid and efficient separation of the particulate or molecular components.

2. Prior Art

There is a growing need in industry for the separation of particles including both cell-size particles and those of submicron and macromolecular size, such as various viruses, latices and polymers. Various methods have been proposed, but in general, they have been too slow, too low in throughput, too complicated, inefficient, expensive or have failed to effect the separation with the desired degree of resolution needed for commercial operations.

Some of the best techniques disclosed have been those based on field-flow fractionation as disclosed in U.S. Pat. Nos. 3,449,938, 4,147,621 and 4,250,026. Other references include Giddings, Anal. Chem. 57945 (1985), and Giddings et al Sep. Science and Tech. 18 (3) 293–306 (1983). These prior known methods, however, are limited in throughput as they are batch techniques that do not operate normally on a continuous basis. They are designed as analytical-scale techniques and they fail to resolve adequate quantities of material needed for many applications.

It is an object of the invention, therefore, to provide a new and efficient process for the fractionation of particulate or molecular components and/or the concentration or purification of such components. It is a further object to provide a new process for fractionation of particles based on the different equilibrium positions or distributions they assume across the thickness of a thin channel when subject to special driving forces. It is a further object to provide a new process for the separation of particles from fluid media which can be accomplished in a rapid and efficient manner. It is a further object to provide a new process for particle fractionation which permits good resolution of separation. It is a further object to provide a process for separation of particles from fluid media which can be operated in a continuous manner. It is a further object to provide a new process for particle fractionation which permits separation on a single pass through the apparatus. It is a further object to provide a new separation process which is economical to operate and uses inexpensive equipment. It is a further object to provide a new type of apparatus for the separation of particles which can be operated singly or in combination with other types of separation equipment. These and other objects will be apparent from the following detailed description thereof.

SUMMARY OF THE INVENTION

It has now been discovered that these and other objects can be accomplished by the new process of the present invention which comprises a rapid and efficient continuous process for the fractionation of particulate or molecular components or the concentration or purification of said components in a special separation channel or cell.

The new process broadly comprises introducing a stream of fluid containing the particulate or molecular components to be separated or concentrated into the inlet end of a thin enclosed channel whose transverse dimension is very small, preferably much smaller than the other 2 dimensions, applying a special field or gradient or combination thereof transversely across the thin dimension of the channel to establish a driving force a component of which is perpendicular to the main flow plane, adjusting the flow rate to achieve laminar flow conditions throughout the channel or at least throughout a sufficient portion of the channel immediately proceding the outlet end to allow the particulate or molecular components under the influence of the field/gradient to segregate into different stream laminae as they approach different transverse equilibrium positions or distributions, splitting the channel stream at the outlet end into substreams containing different separated, purified or concentrated fractions of the particulate or molecular components in the sample mixture, recovering the substreams and thereby recovering the separated or concentrated components of the initial mixture.

It has been surprisingly found that this new process solves many of the defects of the prior known techniques and presents for the first time an efficient and simple process for the continuous separation of particles and molecules based on the different transverse equilibrium distributions they assume under the influence of special driving forces. The process can be operated on a continuous basis while most prior known techniques have been limited to batch operations. The new process is very time efficient and effects many of the desired separations on a single rapid pass through the channel or through a group of such channels, while prior known techniques sometimes require many repeated operations to obtain the desired separation. Further, the new process effects a high degree of resolution for a continuous method. An additional advantage of the new process is that it is effective in separating in a single continuous operations a considerable number of different types of particles. Furthermore, the separation process is very economical in operation as it involves inexpensive equipment with low cost operation and maintenance.

Particularly superior results are obtained in many cases by a further special embodiment involving a process for separation of particles using at least one of the above-described channels linked to one or more additional channels of the same or different type wherein the channels are joined by fluid streams in which one or more of the outlet streams from one or more channels is fed to the inlet streams of one or more other channels.

As used herein the expressions "equilibrium" and "Steady state" refer in a generic sense to the state wherein the concentration distribution of particulate or molecular components along the transverse axis remains constant although individual particles may be changing their position due to Brownian movement.

As used herein the expression "particles" refers in a generic sense to all those particulate or molecular components subject to separation by the presently described method.

As used herein "channel" and "cell" are used to mean the same thing. They refer to a single relatively homogeneous separation unit with their own inlet and outlet port(s) and splitter means(s).

The new process of the invention is conducted in a newly designed and quite different apparatus broadly comprising a cell or channel system formed between 3 sets of opposing walls, top and bottom, side walls and an inlet end wall and outlet end wall, the thickness of the channel being very thin, inlet port means for introducing the fluid stream containing the particles to be separated at the inlet end, at least one means at the outlet end of the channel for splitting the flow into substreams and permitting removal and separate recovery of the substreams, and means for effecting a field or gradient a component of which lines along the transverse axis perpendicular to the planes of the flow laminae which exerts a driving force on the particles.

As special embodiments, the invention provides variations of the above-noted apparatus wherein there are a plurality of physical splitter means, e.g. from 2 to 6, with accompanying outlet ports, said means being at the outlet end or at intermediate positions along the length of the channel.

As a further special embodiment to the apparatus of the invention one or more of the above-noted channels or cells can be joined by fluid streams in various arrangements to effect the separation of additional particle fractions.

DESCRIPTION OF THE DRAWINGS

The various objects and features of the present invention will be more fully understood by reference to the accompanying drawings.

DESCRIPTION OF THE PROCESS

In normal operation the stream of liquid carrying the particles will enter the channel by means of an inlet port and spread out over the cross section of the channel. As the particles are carried along the flow axis of the channel by the fluid stream, they are simultaneously subjected to a driving force acting along the transverse axis. This driving force must be of such a nature and applied at a sufficient level of strength to force the particles to migrate transversely into distinct transverse equilibrium distributions. The equilibrium distributions for the different fractions requiring separation must be sufficiently different that a useful level of fractionation, concentration or purification is realized along the transverse axis. By this it is meant that the distributions of the fractions may not overlap entirely and although some overlap along the transverse axis is allowed, it is generally preferable if the different distributions do not overlap appreciably.

Figure 5:
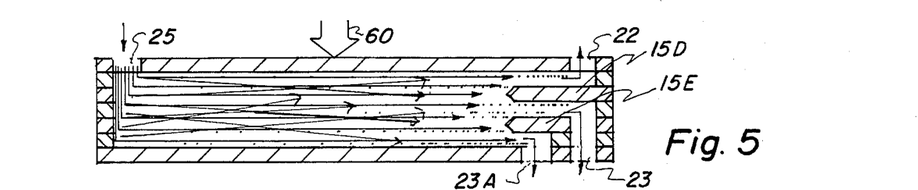
FIG. 5 is a schematic sideview of the channel showing an operation wherein different particle fractions approach different equilibrium positions distributed transversely across the channel thickness, nor just near the walls, and in which the fractions are removed at a plurality of outlet ports.

These distributions can be approached only under laminar flow conditions. Consequently, laminar flow conditions must prevail throughout a sufficient portion of the channel preceeding the inlet to allow time for the particle fractions to segregate or partially segregate as they approach their different equilibrium distributions. At the outlet, the flow splits in such a way that the laminae containing predominately one particle fraction is split away from the lamina containing other particle fractions. Consequently, the flow is split at different appropriate locations along the transverse axis. A split into two substreams can be affected by directing the flow into a triangular end piece as illustrated in FIG. 2A and removing the upper laminae through a small hole drilled in the upper wall at the apex of the triangle and the lower laminae can be similarly removed through a small hole or port in the lower wall. In order to prevent any mixing of the laminae as they pass through the triangular end piece and into the two ports, it is sometimes useful to use a physical splitter means, by which we mean a thin physical structure located at some desired position along the transverse axis and acting to divide the oncoming stream into substreams, one passing above the physical splitter means and another passing below said means. A single physical splitter means at the channel outlet is illustrated in FIG. 2; the simultaneous use of two physical splitter means is illustrated in FIG. 5.

We note that it is important in the above operation to use channels which are thin along the transverse axis in order to maintain laminar conditions and in order to increase the speed with which the particles approach their equilibrium distribution. When particles approach their equilibrium distribution rapidly, they can be swept rapidly through the channel and through the splitter means for rapid particle recovery. Limitations on reducing channel thickness are imposed by the difficulty of interposing physical splitter means within a narrow channel space and of maintaining equilibrium distributions with minimal overlap when the channels are too thin. A compromise thickness will typically lie in the range from 0.1 mm to 5.0 mm.

Figure 1:
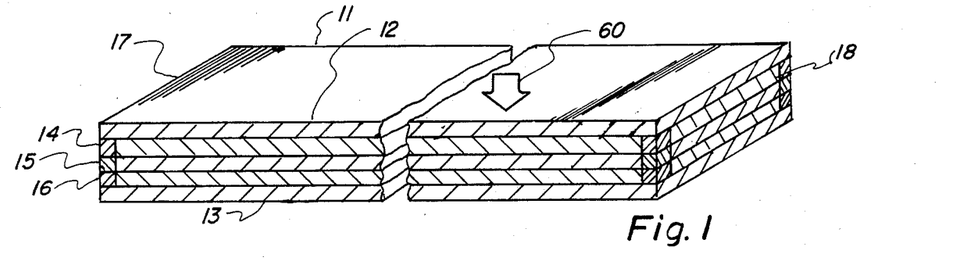
FIG. 1 is a perspective view of the thin elongated flow channel in this case constructed as a sandwich of individual spacer layers of a type which can be used in the process of the invention.

With reference to FIG. 1, the thin elongated channel or cell 11 comprises a top wall 12, bottom wall 13, inlet end 17 and outlet end 18, and spacer layers 14, 15 and 16 to create the desired channel volume and physical splitter means. Only one spacer layer is needed if a physical splitter means is not used. The presence of the transverse driving force is shown as 60 and is generally applied over most or all of the channel volume.

Figure 2:
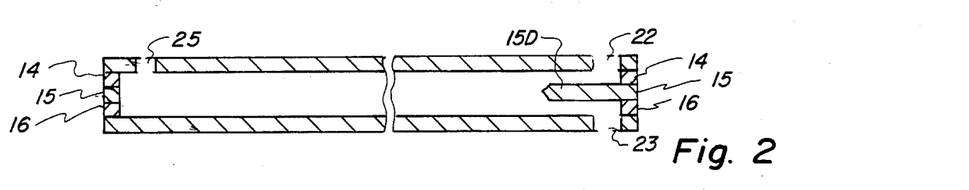
FIG. 2 is a sideview of the channel showing the inlet and outlet ports and a physical splitter means.
Figure 2A:
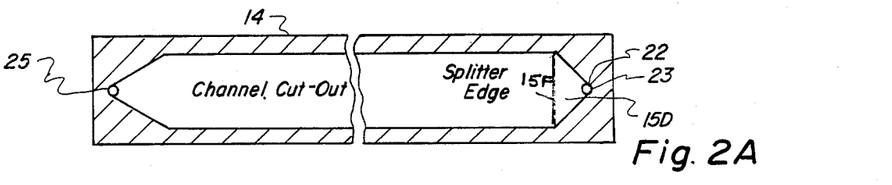
FIG. 2A is a top view of the thin channel showing the cut-out of the thin spacers needed to form the channel volume and the location of a physical splitter means formed from one of the spacers.

FIG. 2 is a side view of the channel showing the inlet port 25, the physical splitter means 15D and outlet ports 22 and 23. FIG. 2A is a top view of the channel showing the cutout volume, the inlet port 25, outlet ports 22 and 23 and the physical splitter 15D and the position of the splitter edge 15F.

Figure 3:
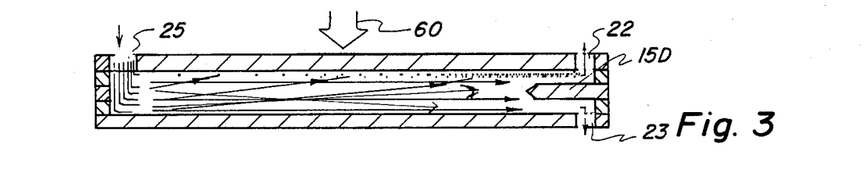
FIG. 3 is a side view of the channel showing the operation wherein one particle fraction approachs an equilibrium position or distribution near the upper wall.

In the general operation of the process, the fluid stream containing the particles is introduced at inlet port 25 and passes along the channel where under the influence of the driving force 60 the particles in the stream segregate into different sets of flow laminae as they approach different equilibrium distributions. In FIG. 3, the equilibrium distribution for one particle fraction is concentrated near the upper wall; consequently this particle type will accumulate at or near the upper wall and will be carried by the flow stream above the splitter means 15D and drawn off through outlet port 22. The other particle fractions will be distributed widely across the channel equilibrium and may be drawn off through both outlet ports 22 and 23. Those drawn off through outlet port 23 will be purified by virtue of the absence of particles from the first fraction.

Figure 4:
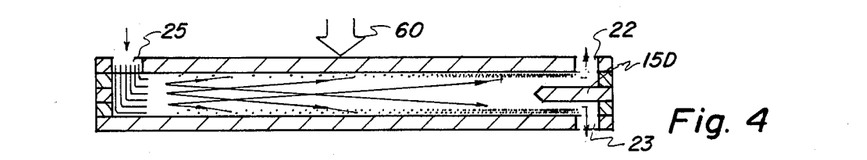
FIG. 4 is a schematic side view of the channel illustrating the operation in which one particle fraction approaches an equilibrium position or distribution near one wall and another particle fraction approaches an equilibrium position or distribution near the other wall.

In a second mode of operation of the process as shown in FIG. 4, the fluid stream containing the particles is introduced at 25 and passes along the channel where under the influence of the driving force the particles segregate into two different sets of flow laminae, one fraction accumulating near the upper wall and the other fraction accumulating near the bottom wall. After stream splitting, the upper substream contains the particles from the first fraction and the lower substream contains the particles from the second fraction.

Figure 6:
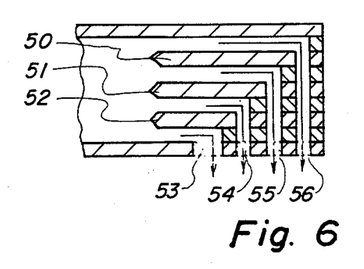
FIG. 6 is a side view of one type of outlet end of such a channel illustrating the use of three physical splitter means and four different outlet ports.

In a third mode of operation shown in FIG. 5, the particles in the fluid stream possess a plurality of equilibrium positions or distributions and thus they begin to accumulate in different laminae upon passing throughout the length of the channel. As shown in that Figure, the flow stream is split into three substreams containing three different particle fractions by means of physical splitter means 15D and 15E and the resulting substreams are removed at outlet ports 22, 23 and 23A. More physical splitters can be used if there are more particle fractions requiring separation. If desired, a larger number of fractions can be simultaneously and continuously collected by using a plurality of splitter means and outlet ports as shown in FIG. 6. In this Figure, the multiple splitter means are shown as 50, 51 and 52 and the multiple outlets as 53, 54, 55 and 56.

Of the above-noted three modes of operation, the second is most preferred. In the second mode, different particles can be directed toward equilibrium positions at the two different walls in a number of ways. For example, if sedimentation forces are used, the density of the carrier can be adjusted to be intermediate between that of the two populations which one desires to separate; in this case, the population or fraction of highest density will accumulate at the lower wall and the population or fraction of lowest density will accumulate at the upper wall. Likewise, in an electrical field, if the carrier is adjusted to have a pH between the pI values of the particles or molecules requiring separation, one of the two desired particle populations will acquire a positive charge and migrate towards one wall while the other population or fraction will acquire a negative charge and migrate towards the other wall. Similarly, by using walls consisting of semipermeable membranes and/or frits, a cross-flow stream moving slowly across the channel thickness at right angles to the flow occuring along the channel axis can be instituted. In this case, one can balance the effect of the cross-flow, which is tending to carry particles toward one wall, and sedimentation, which is arranged to propel particles toward the opposite wall. By adjusting the cross-flow rate, particles can be split into two populations or fractions depending on their sedimentation coefficient, one accumulating at one wall and another accumulating at the opposite wall. In a similar way, one could use a balance between cross flow and electrophoresis where the electrophoresis replaces sedimentation.

Figure 7:
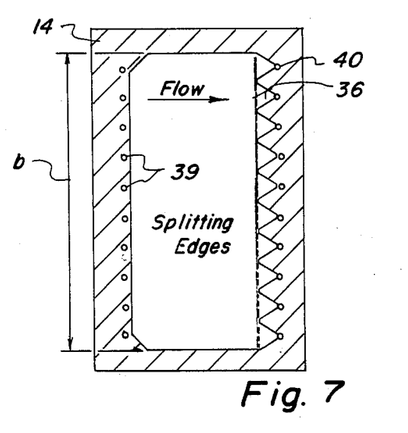
FIG. 7 is a top view of a thin channel illustrating the use of a series of inlet and outlet meansas well as a series of physical splitter means to allow operation in a wider channel having increased capacity.

The throughput of the different cells described above will be relatively high despite the small cell volumes because of the short transit times and the continuous operation. Throughput can be increased further by using banks of such channels working in parallel or by increasing channel breadth as illustrated in FIG. 7. In FIG. 7, the inlet means is illustrated by 39 and the outlet means by 40. The edge of the outlet splitter means is illustrated by 36.

Figure 8:
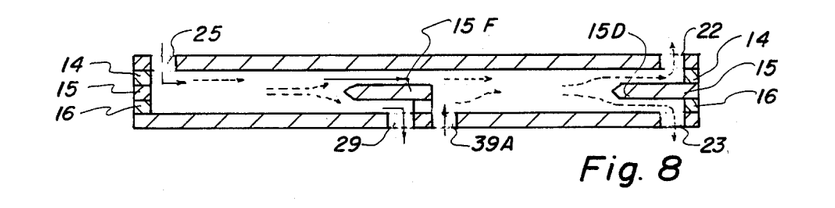
FIG. 8 is a schematic side view illustrating the linkage of two cells within the same structure.

The single-channel systems described above can be expanded in another way to achieve the separation of multiple fractions instead of just two or to separate selected fractions from adjacent fractions having very similar properties. Instead of using a multi-split outlet to a single cell, one can link together a number of separation cells or one or more such cells with other related cell types to form a single integrated separation network or apparatus. An example is illustrated in FIG. 8. In this Figure, the flow stream encounters an intermediate (rather than terminal) physical splitter means 15F after passage through the first part of the separation channel. The intermediate splitter shunts the lower stream out of the channel port 29 for collection or further processing but retains the upper stream, simply transfering it through the splitter region to emerge as sample input stream for the second part of the separation unit. This stream can be joined by a new fluid stream entering input port 39A to assist in establishing the necessary conditions for the second separation. These conditions can be adjusted to achieve separation around another critical valve of the property which determines which wall the particles will migrate to, different from that utilized to divide the particles in the first part of the flow channel. By adjusting the conditions so that the two critical valves lie close to one another, a very narrow fraction can be collected at outlet port 23.

The above examples barely begin to illustrate the numerous possibilities with linked-cell systems. Different separation cells can be distributed as desired over an extended 3-dimensional matrix. The matrix, by way of example, could be formed from a large number of thin spacer layers, each with sections cut-out in such a manner that the interconnected cells are formed in proper relationship to one another. Different substreams from one cell could, for example, be diverted sideways to different locations, each to enter its own cell or series of cells specially designed for processing that substream. Thus various sample containing streams and substreams could be divided, merged with other streams, recirculated and/or introduced into other cells at different levels. In short, the sample containing streams could be directed through mazes of cells of arbitrary structure and complexity. This design freedom would be supported by the natural versatility of "plumbing" in thin-cell systems composed of mutilayers of thin spacer material. Substreams could cross one another at different levels and they could pass through small apertures in other layers to reach different lateral positions. In general, they could conduct fractions around rather freely over the 3 dimensional structure containing the various split cells.

Figure 9:
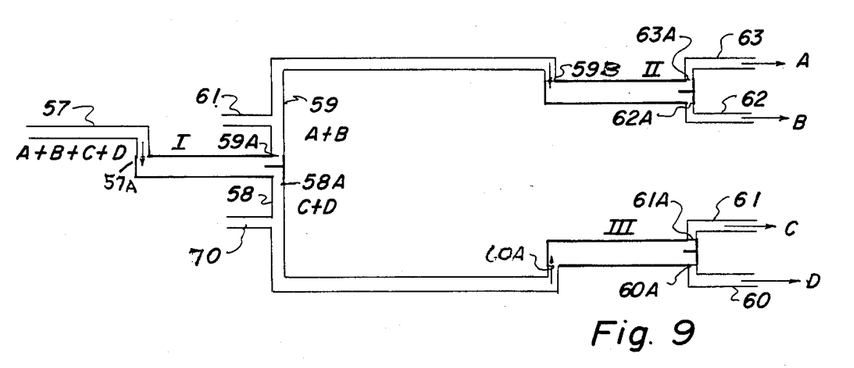
FIG. 9 is a schematic side view illustrating the linkage of several separate cells.

A simple system of three linked cells, each containing a different structural unit is illustrated in FIG. 9. Here the feed containing particle fractions A,B,C and D enters channel I from feed line 57 to port 57A and upon passage through that channel is divided into two streams, the upper stream containing fraction A and B and the lower stream containing fractions C and D. The upper fraction containing A and B is taken out outlet 59A through line 59 where it is combined with fluid of a different composition from line 61 so as to establish appropriate conditions for the subsequent fractionation to be carried out in channel II. The combined mixture is taken through line 59 to inlet port 59B of channel II. The lower fraction containing C and D is taken out outlet 58A through line 58 where it is combined with fluid of a different composition from line 70 so as to establish appropriate conditions for the fractionation to be carried out in channel III. The combined mixture is taken through line 58 to inlet port 60A of channel III.

When the merged upper stream enters inlet port 59B and flows through channel II, the separation conditions are such that fraction A and fraction B are separated and emerge in separate substreams. Fraction A is removed at outlet 63A and taken off through line 63, and fraction B is removed at outlet 62A and taken off through line 62. Likewise, the merged lower stream enters inlet port 60A and flows through channel III where the separation conditions are such that fraction C and fraction D are separated and emerge in separate substreams. Fraction C is removed at outlet 61A and taken off through line 61, and fraction D is removed at outlet 60A and taken off through line 60.

The separations in channel II and III occur on the basis of different critical values of the determining property, which critical values are adjusted by varying the composition and flow rate of the merging fluid streams 61 and 60. For example, streams 60 and 61 can be adjusted to provide the necessary density or pH in sedimentation or electrical field systems, respectively, of fluid entering channels II and III, to control the critical density or pH values of particle fractions, above which particles go to one wall and below which they go to the opposite wall.

The example of linked but independent channel structures as illustrated in FIG. 9 is also subject to extensive expansion and variability to fit different separation needs. A direct expansion of the scheme shown in FIG. 9 would entail feeding each of the four particle fractions into a subsequent set of four channels such that each of the fractions could again be split into two parts thus yielding a total of 8 fractions. This scheme could be continued to incorporate additional separation channels or other schemes could be utilized to accomodate other needs. The dimensions of each channel could be varied in order to accomodate the different sample loads passing through the channel. Different transverse driving forces, e.g. electrical and sedimentation, could be applied to different channels within the linked system. It should be noted that the two or more substreams emerging from any such channel can have their relative flow rates adjusted by various flow control means in order to accomodate variable sample loads and in order to optimize separation conditions.

DETAILS OF THE INVENTION

The type and size of the particles to be separated may vary over a wide range depending on whether the type and strength of the field applied can provide an adequate driving force for separation. The particles may in some cases be as small as polypeptides and as large or larger than most biological cells. Preferably, when gravity provides the driving force, the particles should range in size from about 1 um to 100 um. The particles may also vary as to density and shape, and the conditions of the separation process will be adjusted accordingly.

The particle fractions to be separated should, of course, have different equilibrium positions or distributions across the thickness of the thin channel so that the desired separation can be effected according to the process of the invention.

The fluid in which the particles to be separated are contained may also vary over a wide range. In some cases, the fluid will be that in which the particles are normally prepared or contained, such as aqueous buffers for biological particles. In other cases, the particles are contained in specially prepared fluids or solutions in which the density, pH or other fluid characteristics are controlled in order to optimize the separation.

The concentration of particles in the feed stream may also vary widely from extreme dilutions up to about 30% or more. In most cases, the concentration will vary from about 0.1% to about 10%.

In some cases, additional fluids can be introduced with the fluid containing the particles. Such second solutions may contain modifiers (such as density modifiers, pH modifiers, etc. to shift equilibrium and increase resolution and throughput. Such fluids may be any liquid, such as water, butanol, etc.

The fields or gradients used singly or in combination to establish the transverse driving force to effect the movement of particle fractions to different transverse equilibrium positions include, among others, sedimentation fields caused by gravitation or centrifugation, electrical fields, dielectrical fields, cross flow forces, density gradients, pH gradients, concentration gradients, and the like. Combination of one or more such fields or gradients can be used as desired or necessary. Preferred field/gradients or combination thereof include sedimentation fields including both gravitation and centrifugation, electrical fields, dielectric fields, pH gradients with electrical fields, density gradients with sedimentation fields, sedimentation fields with cross flow forces and electrophoresis with cross flow forces.

The strength of the field of gradient applied to the channel may vary depending upon many factors, such as particle mobility, thickness of separation cell, fluid density, etc, and is best determined for each individual case. Generally, the highest practical field strength is preferred because speed and throughput usually increases with field strength.

The temperature employed in the separation process may vary over a wide range, but generally will range between about 0° C. to about 25° C.

The rate of introducing the above-noted substreams, some containing the particles and some not, may vary over a wide range. In general, the rate of introduction of the substreams will vary from about 0.1 ml/min. to about 100 ml/min. As noted above, the flow rate is adjusted in each case so as to achieve the necessary laminar flow conditions throughout the channel or at least over a sufficient length of channel immediately preceding the outlet end to allow the particulate or molecular fractions under the influence of the driving force to segregate into different stream laminae as they approach different transverse equilbrium positions. This adjustment will depend on the above-noted factors and can best be determined for each individual case.

The particle fractions obtained by the above-noted process will be recovered at the various outlet means in the form of fluid solutions or suspensions, which may be used directly as such or which may be subjected to further separation or concentration means, such as centrifugation or evaporation, to thereby recover the particles themselves.

The apparatus to be used in the process of the invention may be constructed in a variety of ways with a variety of different materials and sizes as long as it provides the channel of the necessary thickness, the desired number of inlet and outlet means, the desired number of splitter means, pumping means, flow control means and means for applying the desired transverse driving force.

The thickness of the channel along which dimension the segregation takes place should be very thin to enhance speed and laminar flow, and preferably less than five millimeters. Particularly good results are obtained when the thickness varies from about 0.1 mm to about 2 mm. In some cases, especially good results are obtained when the thickness is very thin compared to the other two dimensions of the channel.

The length and breadth of the channel may vary over a wide range. Increasing the length and breadth of the channel is sometimes desirable in order to increase throughput.

The channel should posses an inlet means for introducing the fluid substream containing the particles to be separated. Such means, which may be ports or holes with or without pump means, may be located at the top or bottom of the inlet end or at the end of the separation cell as determined by convenience.

It is also possible to employ an additional inlet means for the introduction of fluid material needed to effect or assist in effecting the desired separation into the respective equilibrium positions. However, the additional fluid stream can generally be mered with the particle-containing feed stream.

The channel also possesses at least one splitter means at the outlet end of the channel, and in some cases a plurality of such splitter means depending upon the intended operation of the channel. Preferably, such splitter means at the outlet end may vary from about 1 to 6.

In some cases, particularly in those instances where additional fluid streams are introduced to assist in the separation, splitter means can also be employed at the inlet end.

As noted, improved results are obtained in many cases by employing splitter means at intermediate locations along the length of the channel as shown in FIG. 8. These splitter means may also vary in number, e.g. from 1 to 6, depending upon the intended operation.

The splitter means, wherever located, may be of any desired shape and size as long as they accomplish the purpose of splitting the channel stream into substreams containing pysically distinct laminae. As noted above, the generic expression "splitter means" refers to all such means, including specifically placed outlet ports, physical barriers, and the like. "Physical" splitter "means as used herein refers to an actual physical barrier as shown by 15D in FIG. 2.

The preferred physical splitter means are best prepared from very thin material, such as plastic or metal sheeting and need extend only a short distance into the cell, e.g. 1–3 cm. They preferably extend through the tapered or triangular end regions of the cell so as to facilitate a clean separation of laminae.

The channel may be constructed of thin spacer layers of various materials from which regions are cut out to create the channel space. Interior spacer elements not adjacent to a channel wall can be cut in such a way that extra area (such as 15D in FIG. 2A) is left intact to form a physical splitter means. Thus, for the creation of two outlets for two substreams, one would normally use three spacer elements, where the center one would be cut to form the physical splitter means. These elements can be cut to different shapes and sizes as long as they collectively provide a uniform channel with the necessary splitter means. In most cases, it is desirable to cut triangular shaped pieces from the ends of the spacers not used for physical splitter means to permit a smooth transition from the channel flow to the narrow inlets and outlets at the apices of the triangles as shown in FIG. 2.

The channel top and bottom walls are best constructed of rigid materials with a smooth inert surface.

In the event cross flow is used to generate part of the driving force, the top and/or bottom walls must be a permeable or semipermeable material. The spacer and physical splitter elements may be constructed of any suitable material, e.g. from thin plastic materials, such as mylar, teflon, polycarbonates, and the like, or from thin sheets of metal, such as stainless steel, etc.

SPECIFIC EMBODIMENT OF THE INVENTION

A specific embodiment of the new process and apparatus of the present invention is illustrated below.

A thin channel made of stainless steel walls and a single mylar spacer element and having the dimensions of 90.5 cm×2 cm×0.25 mm (thickness) was coiled and inserted in a centrifuge basket. Special seals like those used in sedimentation field flow fractionation were employed to supply the feed stream which entered at a port at the inside wall at the tip of the triangular end piece at the inlet end of the channel. The feed stream consisted of a 20% by weight solution of sucrose in water with a density of 1.08 grams per milliter and a mixture of 0.822 micrometer polystyrene heads and 0.586 micrometer polymethyl methacrylate beads. The latter were used at very low concentrations of 0.003% and 0.0025% respectively because of the high cost of these materials. The respective densities of the materials are 1.05 and 1.2 grams per milliter, values which lie on either side of the 1.08 grams per milliter density of the carrier solution. Consequently with the channel rotating at a spin rate of 500 rpm the polystyrene heads migrated towards their equilibrium position at the inner wall and the polymethyl methacrylate beads migrated toward their equilibrium position at the outer wall.

At the outlet of the channel, the flow stream was forced into a triangular end piece at the apex of which two holes were drilled one at the inside and one at the outside. Because of their respective equilibrium positions, the polystyrene beads exited through the inner port while the polymethyl methacrylate beads exited through the port in the outer wall using a total flow rate of 0.47 milliters per minute split approximately equally between the two outlets.

Samples were collected from the two outlet streams and analyzed by an electron microscope where the two different materials could be distinquished readily by virture of the observable difference in bead size. While there was some cross-contamination which could almost certainly be reduced by a physical splitter means the substream collected from the outer wall was observed to contain 94% polymethyl methacrylate beads while the substream collected from the port at the inner wall was observed to contain 82% polystyrene beads. Somewhat better results were observed when the flow rate of the outlet substream from the inner wall was controlled to a value 1.6 times larger than the flow rate from the outer wall. In that case 95% of the beads exiting the outer wall substream were polymethyl methacrylate and 87% of the beads exiting the inner wall substream were polystyrene.

The process and apparatus described in the present application are complementary to, and in some respects they are superior to, the process and apparatus described in my copending application. The two procedures described in these applications are complementary in the sense that fractionation occurs based on increments in different particle properties in the two cases. In the earlier application, separation is based primarily on differences in transport rates whereas in the present application separation is based on differences in equilibrium positions. For example, using sedimentation as a driving force, separation in the earlier application would be based on differences in sedimentation coefficients which depend primarily on particle size and secondarily on particle density. In the present invention, separation using sedimentation forces depends entirely on differences in particle density. Therefore the choice between the two systems depends upon whether one wishes to fractionate particles primarily according to differences in size or according to differences in density. Both cases are important in many different industrial applications. In general, a choice between the two methods of these applications depends upon processing requirements and goals.

In some respects, the present apparatus is superior to those described in the earlier application because the apparatus is simpler and subject to less restrictive requirements. For example, no inlet splitter is required in the present invention, also large flow variations can be tolerated and less channel uniformity is required. In the present case flow distortions at the edges and ends of the channel are relatively unimportant. As a consequence of these less stringent requirements the present invention can be carried out with somewhat simpler and less expensive apparatus than those described in the previous copending application.

I claim as my invention:

1. A process for fractionating, concentrating and purifying particles contained in (the) a liquid stream which comprises
   a. continuously introducing a stream of liquid containing the particles to be separated into an inlet end of a thin enclosed channel, said channel having said inlet end and an outlet end and having a thickness of less than about 5 millimeters along a transverse axis perpendicular to the main flow plane of said channel,
   b. applying a field or gradient selected from the group consisting of gravitation, centrifugation, dielectrical field, electrical fields, cross flow forces, density gradients, pH gradients and concentration gradients and combinations thereof, transversely across the thin dimension of the channel to generate a driving force whose direction or a component thereof lies along the transverse axis perpendicular to the main flow plane,
   c. adjusting the flow rate to achieve laminar flow conditions throughout the channel or at least throughout a sufficient portion of the channel immediately preceding the outlet end to allow the particle fractions under the influence of the field or gradient to wholly or partially segregate into different stream laminae as they approach different transverse equilibrium distribution,
   d. splitting the channel stream at the outlet end into substreams containing different fractions of the particles,
   e. recovering the separate substreams and thereby recovering the separated, concentrated (or) and purified fractions of the particles contained in the initial liquid stream.

2. A process as in claim wherein one particle fraction in the liquid stream in the channel approaches an equilibrium distribution positioned near one wall of the channel and the substream composed of the laminae near said wall which is concentrated in said fraction is removed from the outlet end of the channel, leaving all other outlet substreams free of said particle fraction and thus purified with respect to said fraction.

3. A process as in claim 1 wherein the particles in the liquid stream in the channel separate along the transverse axis, one fraction approaching an equilibrium distribution positioned near one wall of the channel and another fraction approaching an equilibrium distribution positioned near the opposite wall, following which the channel stream is split into two substreams each containing one of the two particle fractions, the substreams then being removed with their separation fractions from the outlet end of the channel.

4. A process as in claim 1 wherein the particles in the liquid stream in the channel separate and approach a plurality of equilibrium positions across the thickness of the channel and the laminae corresponding thereto are separated and removed with their separate fractions from the outlet end of the channel.

5. A process as in claim 1 wherein the thickness of the channel lines between about 0.1 mm and 5.0 mm.

6. A process as in claim 1 wherein there are two or more of the described separation channels joined by liquid streams to which streams new liquid is added in which one or more of the outlet substreams from each said channel is fed to the inlet of at least one other channel.

7. A process as in claim 1 wherein physical splitter means are employed at the outlet end of the channel to split the outgoing stream into at least two substreams.

8. A process as in claim 1 wherein the driving force is induced by centrifugation.

9. A process as in claim 1 wherein the driving force is induced by gravitation.

10. A process as in claim 1 wherein the driving force is induced by an electrical field.

11. A process as in claim 1 wherein the driving force is derived from a combination of a pH gradient and an electrical field.

12. A process as in claim 1 wherein the driving force is derived from a combination of a density gradient and a sedimentation force.

13. A process as in claim 1 wherein the driving force is a dielectrical force.

14. A process as in claim 1 wherein the driving force is derived from a combination of dielectrical and sedimentation forces.

15. A process as in claim 1 wherein the driving force is derived from a combination of a cross flow force and sedimentation.

16. A process as in claim 1 wherein the driving force is derives from a combination of a cross flow force and an electrical force.

17. A process as in claim 1 wherein at least one means is employed along the length of the channel to split the stream at least at one location along the channel causing at least one of the obtained substreams to enter a subsequent section of the same channel or another channel for additional fractionation, and the remaining substreams to exit the channel for collection.

18. An apparatus for separating mixtures of particles contained in a liquid stream into desired fractions or concentrating particle fractions consisting of a separation cell comprising:
   a. a channel system formed between three sets of opposing walls, an end set of walls comprising an inlet end wall and an outlet end wall, and the thickness of the channel being very thin,
   b. an inlet means for introducing a liquid stream containing the particles to be separated at the inlet end of the channel,
   c. at least one means at the outlet end of the channel for splitting the channel stream into substreams and permitting separate recovery of said substreams,
   d. means for removing the substreams collected at the outlet end of the channel,
   e. means for applying a field or gradient selected from the group consisting of gravitation, centrifugation, dielectrical fields, electrical fields, cross flow forces, density gradient, pH gradient, concentration gradient and combinations thereof, having a gradient direction or at least a component thereof along the transverse coordinate perpendicular to the plane of the flow stream in the channel,
   f. and means for adjusting the flow rate of the liquid stream in the channel to achieve laminar flow conditions throughout the channel or at least throughout a sufficient portion of the channel immediately preceding the outlet end to allow the particle fractions under the influence of the field or gradient to wholly or partially segregate into different stream laminae as they approach different transverse equilibrium distributions.

19. An apparatus as in claim 18 wherein the thickness of the channel lies between about 0.1 mm to 2 mm.

20. An apparatus as in claim 18 wherein there are two or more of the described separation cells joined by liquid streams to which streams new liquid can be added in which one or more of the outlet substreams from each said cell is fed to the inlet of at least one other cell.

21. An apparatus as in claim 18 wherein the inlet end wall and the outlet end wall, within the interior of the channel, converge to a point to form a narrow inlet and outlet port for the ingress and egress of substreams.

22. An apparatus as in claim 18 wherein there are from one to 9 physical splitter means at the outlet end of the channel to split the substreams as they approach the outlet end of the channel.

23. An apparatus as in claim 18 wherein the channel is constructed as a sandwich of thin spacer elements from which the channel volume and said at least one splitting means is created by cutting appropriate volumes and shapes out of each of the said spacer elements.

24. An apparatus as in claim 18 wherein the channel, except in the vicinity of the end walls, is rectangular in shape.

25. An apparatus as in claim 18 wherein at least one means is present along the length of the channel to split the stream at least at one location along the channel causing at least one of the obtained substreams to enter a subsequent section of the same channel or another channel for additional fractionation, and causing the remaining substreams to exit the channel for collection.

* * * * *

UNITED STATES PATENT AND TRADEMARK OFFICE
CERTIFICATE OF CORRECTION

PATENT NO. : 4,737,268

DATED : April 12, 1988

INVENTOR(S) : John C. Giddings

It is certified that error appears in the above-identified patent and that said Letters Patent is hereby corrected as shown below:

Col. 1, line 5, should read:

"Work on this invention was supported by funding from National Science Foundation contract CHE-8218503."

Signed and Sealed this

Eighth Day of October, 1991

Attest:

HARRY F. MANBECK, JR.

Attesting Officer

Commissioner of Patents and Trademarks